(12) United States Patent
Kandori et al.

(10) Patent No.: US 9,072,429 B2
(45) Date of Patent: Jul. 7, 2015

(54) APPARATUS AND METHOD FOR DRIVING CAPACITIVE ELECTROMECHANICAL TRANSDUCTION APPARATUS

(75) Inventors: Atsushi Kandori, Ebina (JP); Masao Majima, Isehara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 621 days.

(21) Appl. No.: 13/050,758

(22) Filed: Mar. 17, 2011

(65) Prior Publication Data

US 2011/0227448 A1   Sep. 22, 2011

(30) Foreign Application Priority Data

Mar. 18, 2010 (JP) ................. 2010-062602

(51) Int. Cl.
*A61B 5/00* (2006.01)
*B06B 1/02* (2006.01)
(52) U.S. Cl.
CPC ............ *A61B 5/0095* (2013.01); *B06B 1/0292* (2013.01)
(58) Field of Classification Search
CPC .......... A61B 8/00; A61B 5/05; A61B 5/0095; B06B 1/0292
USPC .................. 600/407, 475; 367/140
See application file for complete search history.

(56) References Cited

U.S. PATENT DOCUMENTS

| | | | | |
|---|---|---|---|---|
| 4,559,825 A | * | 12/1985 | Martens | 73/622 |
| 4,566,331 A | * | 1/1986 | Schroeder | 73/632 |
| 4,819,652 A | * | 4/1989 | Micco | 600/455 |
| 5,162,724 A | * | 11/1992 | Katayama et al. | 324/76.19 |
| 5,637,090 A | * | 6/1997 | McGee et al. | 600/374 |
| 6,599,248 B1 | * | 7/2003 | Tamura | 600/454 |
| 6,979,292 B2 | * | 12/2005 | Kanayama et al. | 600/437 |
| 7,515,948 B1 | * | 4/2009 | Balberg et al. | 600/323 |
| 2005/0215909 A1 | | 9/2005 | Barnes | |
| 2006/0122475 A1 | * | 6/2006 | Balberg et al. | 600/323 |

(Continued)

FOREIGN PATENT DOCUMENTS

| | | |
|---|---|---|
| CN | 1527414 A | 9/2004 |
| CN | 1929699 A | 3/2007 |

(Continued)

OTHER PUBLICATIONS

Petra, "Applied Physics B", Lasers and Optics DOI 10.1007/s00340-009-3379-1 Feb. 13, 2009.*

(Continued)

*Primary Examiner* — Luke Ratcliffe
*Assistant Examiner* — Hovhannes Baghdasaryan
(74) *Attorney, Agent, or Firm* — Canon USA, Inc. IP Division

(57) ABSTRACT

An apparatus is configured to drive a transduction apparatus including a cell with a first electrode and a second electrode disposed so as to oppose each other via a gap. The apparatus includes a timing detection unit and a control unit. The timing detection unit detects a timing of outputting of an electromagnetic wave from an electromagnetic wave source configured to output the electromagnetic wave to irradiate an object to be measured. The control unit drives and controls the transduction apparatus in synchronization with the detected timing such that the capacitive electromechanical transduction apparatus is put in a receiving state only for a period in which an acoustic wave generated in an inside of the object irradiated with the electromagnetic wave is received.

30 Claims, 6 Drawing Sheets

(56) References Cited

U.S. PATENT DOCUMENTS

| | | | |
|---|---|---|---|
| 2007/0016074 A1* | 1/2007 | Abreu | 600/475 |
| 2007/0093702 A1* | 4/2007 | Yu et al. | 600/326 |
| 2007/0146019 A1 | 6/2007 | Foote | |
| 2007/0252978 A1* | 11/2007 | Van Der Voort et al. | 356/301 |
| 2007/0287912 A1 | 12/2007 | Khuri-Yakub et al. | |
| 2008/0015441 A1* | 1/2008 | Kanda et al. | 600/459 |
| 2008/0221647 A1* | 9/2008 | Chamberland et al. | 607/88 |
| 2008/0294055 A1* | 11/2008 | Adachi et al. | 600/463 |
| 2009/0005685 A1* | 1/2009 | Nagae et al. | 600/459 |
| 2009/0024038 A1* | 1/2009 | Arnold | 600/459 |
| 2009/0036761 A1* | 2/2009 | Abreu | 600/318 |
| 2009/0187099 A1* | 7/2009 | Burcher | 600/430 |
| 2009/0273256 A1* | 11/2009 | Martin et al. | 310/318 |

FOREIGN PATENT DOCUMENTS

| | | |
|---|---|---|
| CN | 101243968 A | 8/2008 |
| CN | 101305903 A | 11/2008 |
| CN | 101535795 A | 9/2009 |
| JP | 63-187137 A1 | 8/1988 |
| JP | 03-123542 A | 5/1991 |
| JP | 06-094689 A | 4/1994 |
| JP | 2001-258879 A | 9/2001 |
| WO | 2006/041114 A | 4/2006 |
| WO | 2006/041114 A1 | 4/2006 |
| WO | 2007-037293 A1 | 4/2007 |

OTHER PUBLICATIONS

U.S. Appl. No. 13/141,488, filed Jun. 22, 2011, Yoshitaka Zaitsu.

U.S. Appl. No. 13/025,869, filed Feb. 11, 2011, Kazunari Fujii.

U.S. Appl. No. 13/012,699, filed Jan. 24, 2011, Atsushi Kandori.

U.S. Appl. No. 13/114,567, filed May 24, 2011, Yoshihiro Hasegawa.

U.S. Appl. No. 13/087,178, Apr. 14, 2011, Yuichi Masaki.

* cited by examiner

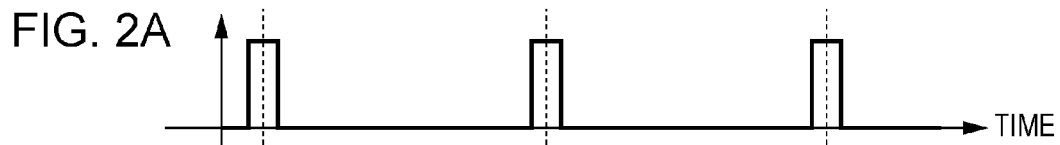
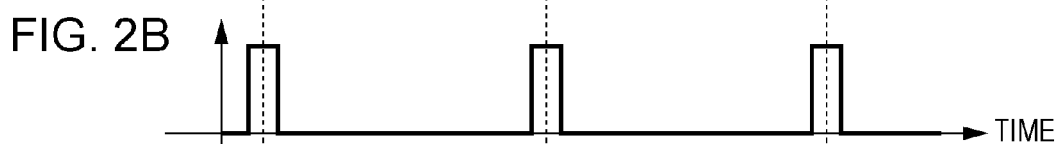
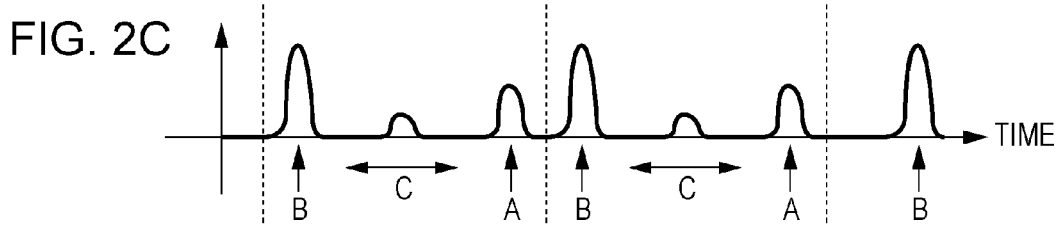
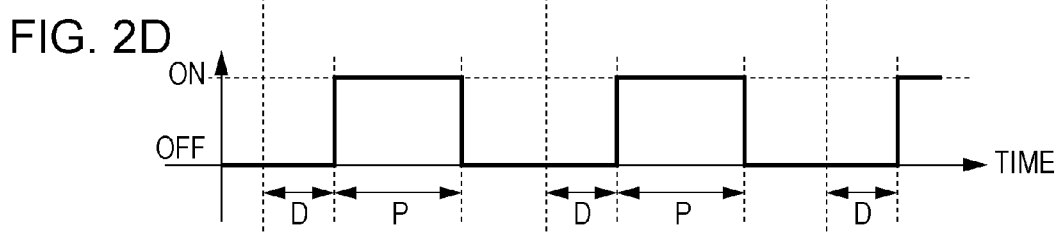
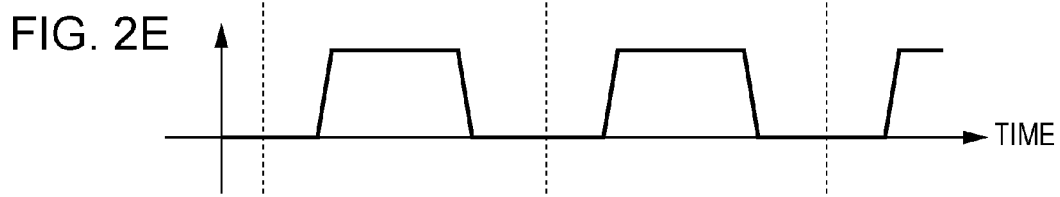
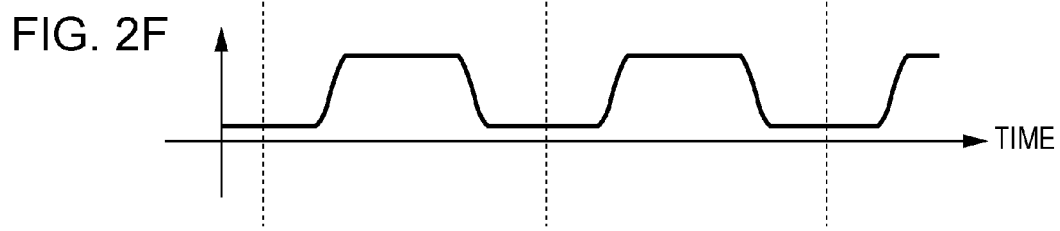

APPARATUS AND METHOD FOR DRIVING CAPACITIVE ELECTROMECHANICAL TRANSDUCTION APPARATUS

BACKGROUND OF THE INVENTION

1. Field of the Invention

The present invention relates to an apparatus and a method of driving a capacitive electromechanical transduction apparatus configured to receive an acoustic wave by a photoacoustic effect. In the present description, the term "acoustic wave" is used to describe a wide variety of acoustic waves including a sonic wave, an ultrasonic wave, and a photoacoustic wave, which are elastic waves generated (by the photoacoustic effect) in an object to be measured when the object to be measured is illuminated with light such as a near infrared ray (electromagnetic wave).

2. Description of the Related Art

An example of an electromechanical transduction apparatus for receiving/transmitting an ultrasonic wave is a CMUT (Capacitive Micromachined Ultrasonic Transducer) that is a capacitive ultrasonic transducer. The CMUT can be produced using a MEMS (Micro Electro Mechanical Systems) process based on a semiconductor process. It has been proposed to use a CMUT as an ultrasonic wave transducer (electromechanical transduction apparatus) in a measurement apparatus using a photoacoustic effect (see, for example, U.S. Patent Application Publication No. 2007/0287912).

To allow an object to be measured to generate an acoustic wave by the photoacoustic effect, for example, high-intensity light with a particular pulse width is periodically emitted by a light source and the object to be measured is illuminated with the emitted light. However, when the object to be measured is a living body, an acoustic wave is also generated by the photoacoustic effect at a skin on a surface of the living body. Furthermore, if another object located in the vicinity of the object to be measured is illuminated with the light, an acoustic wave is also generated by the photoacoustic effect. The acoustic waves generated in the above-described manner may reach an acoustic wave receiving unit. In this case, the acoustic waves received by the acoustic wave receiving unit do not include any information about the object to be measured, and thus the received acoustic waves function as noise. The noise of the acoustic wave originating from light emitted by the light source is greater in magnitude than the acoustic wave generated in the object to be measured (for example, by a light absorber such as a tumor existing in a living body). If such noise is input to the CMUT (serving as the electromechanical transduction apparatus) optimized for a particular magnitude of an acoustic wave generated by the object to be measured, the input noise can exert a great influence on the acoustic wave receiving operation of the CMUT. As described above, noise can cause a reduction in measurement accuracy in measuring an object to be measured.

SUMMARY OF THE INVENTION

According to an aspect of the present invention, an apparatus is configured to drive a transduction apparatus including a cell with a first electrode and a second electrode disposed so as to oppose each other via a gap. The apparatus includes a timing detection unit configured to detect a timing of outputting of an electromagnetic wave from an electromagnetic wave source configured to output the electromagnetic wave to irradiate an object to be measured and a control unit configured to control the transduction apparatus in synchronization such that the transduction apparatus is put in a receiving state only for a period in which an acoustic wave generated in an inside of the object irradiated with the electromagnetic wave is received.

Further features of the present invention will become apparent from the following description of exemplary embodiments with reference to the attached drawings.

BRIEF DESCRIPTION OF THE DRAWINGS

FIGS. 2A to 2F are graphs illustrating driving and controlling operations according to embodiments of the present invention.

DESCRIPTION OF THE EMBODIMENTS

Figure 1:
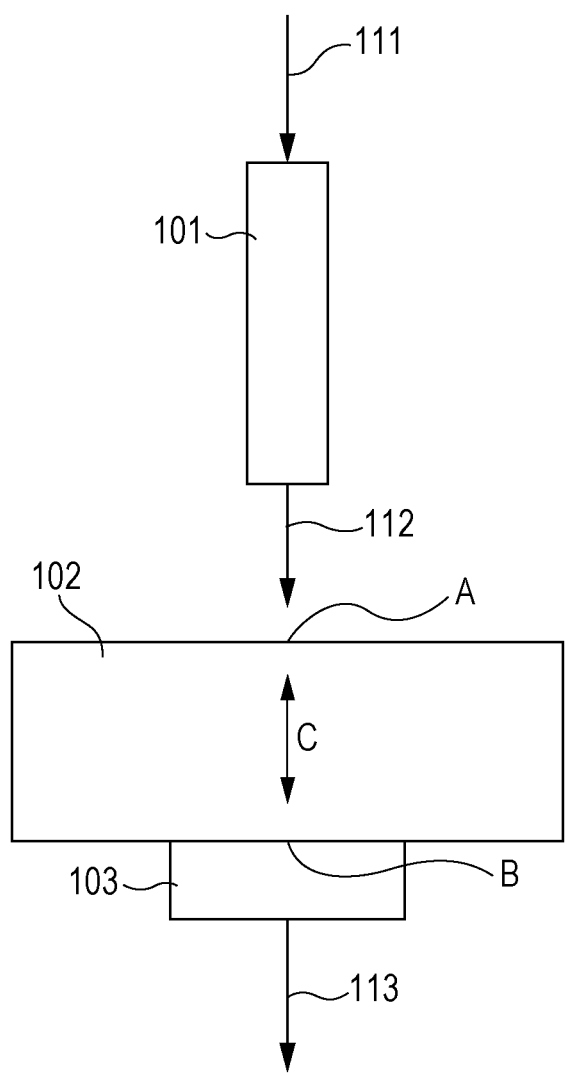
FIG. 1 is a diagram illustrating an acoustic wave measurement system according to an embodiment of the present invention.

The present invention is described in further detail below with reference to embodiments. The present invention relates to an apparatus and a method of driving a capacitive electromechanical transduction apparatus such as a CMUT to receive an acoustic wave in PAT (Photoacoustic Tomography) or the like. For example, when an object to be measured is illuminated with light, there is a possibility that an acoustic wave (surface acoustic wave) with a great magnitude is generated at a surface of the object to be measured. Such a surface acoustic wave or the like can exert an influence on the following an acoustic wave receiving operation. In the present invention, the driving of the capacitive electromechanical transduction apparatus is controlled such that acoustic waves originating from surface acoustic waves or the like are not received and acoustic waves are received after the surface acoustic waves have passed away. More specifically, in the apparatus and the method of driving the capacitive electromechanical transduction apparatus according to the present invention, in synchronization with timing of outputting an electromagnetic wave from an electromagnetic wave source, the electromechanical transduction apparatus is put in a receiving state only for a period in which an acoustic wave generated in the inside of an object to be measured by the photoacoustic effect is received. Based on the above-described basic aspects of the apparatus and the method of driving the electromechanical transduction apparatus according to the present invention, the apparatus and the method may be embodied in various manners as described below.

Typically, the electromagnetic wave source outputs an electromagnetic wave in a pulse form at intervals (for example, periodically). In synchronization with the timing of outputting of the electromagnetic wave, the control unit switches the state of the electromechanical transduction apparatus between a receiving state and a non-receiving state so as to receive only an acoustic wave associated with an object in the inside of the object to be measured illuminated with the electromagnetic wave in the pulse form. Note that the synchronization with the outputting of the electromagnetic wave may be performed such that the switching is performed when a predetermined time has elapsed after the electromagnetic wave was output. Use of the pulse form for the electromagnetic wave makes it possible for the acoustic wave originating from the inside of the object to be measured to travel to the electromechanical transduction apparatus separately from the acoustic wave originating from the surface of the object to be measured, and thus it becomes possible to selectively detect only the acoustic wave originating from the inside of the object to be measured.

Now, embodiments of the apparatus and the method of driving the capacitive electromechanical transduction apparatus according to the present invention are described below with reference to the accompanying drawings. In the embodiments described below, it is assumed by way of example that an upper electrode serves as the second electrode to which a bias voltage is applied, while a lower electrode serves as the first electrode from which an induced current is output. Note that the roles of the upper electrode and the lower electrode may be exchanged. In some embodiments described below, it is assumed by way of example that the timing detection unit is disposed in the DC potential application unit or the current detection unit so that the timing detection unit detects the timing of outputting of the electromagnetic wave based on the received driving signal of the electromagnetic wave source. Alternatively, the timing detection unit may be disposed outside the DC potential application unit or the current detection unit so that the timing detection unit receives a part of the electromagnetic wave emitted from the electromagnetic wave source and detects the timing of outputting of the electromagnetic wave based on the received electromagnetic wave. In some embodiments described below, it is assumed by way of example that the control unit is also disposed in the DC potential application unit or the current detection unit and the control unit drives the electromechanical transduction apparatus according to a detection result provided by the timing detection unit such that the electromechanical transduction apparatus is put in the receiving state only for the period in which the acoustic wave generated in the inside of the object to be measured. Alternatively, the control unit may be disposed outside the DC potential application unit or the current detection unit and the control unit may control the DC potential application unit or the current detection unit.

First Embodiment

An apparatus and a method of driving the electromechanical transduction apparatus according to a first embodiment are described below. In this embodiment, the electromechanical transduction apparatus is driven in synchronization with periodic emission (pulsive emission) of an electromagnetic wave that can provide the photoacoustic effect such that the electromechanical transduction apparatus is put in the acoustic wave receiving state only for a period in which an acoustic wave generated inside an object to be measured is received while, for the other period, absolutely no acoustic wave is received or the reception sensitivity is reduced such that substantially no acoustic wave is received.

In FIG. 1 illustrating a configuration of an acoustic wave measurement system according to the first embodiment of the present invention, reference numeral 101 denotes a light source that radiates an electromagnetic wave, reference numeral 102 denotes an object to be measured, and reference numeral 103 denotes an ultrasonic wave transducer serving as an electromechanical transduction apparatus. Reference numeral 111 denotes a driving signal that drives the light source 101, reference numeral 112 denotes output light (pulsed light) that is the electromagnetic wave output from the light source 101, and reference numeral 113 denotes a detection signal detected by the ultrasonic wave transducer 103. A principle of the driving-and-controlling operation according to the present embodiment is described below referring to FIGS. 2A to 2D illustrating timings associated with the acoustic wave measurement system. In each of FIGS. 2A to 2F, a horizontal axis represents a time. Vertical axes represent the magnitude of the driving signal 111 in FIG. 2A, the intensity of light 112 output from the light source 101 in FIG. 2B, and the magnitude of the detection signal 113 of the acoustic wave detected by the ultrasonic wave transducer 103 in FIG. 2C. In FIG. 2D, a vertical axis represents whether the ultrasonic wave transducer 103 is in the receiving state (ON-state) or the non-receiving state (OFF-state).

The light source 101 is located so as to oppose the ultrasonic wave transducer 103 via an object to be measured 102. Hereinafter, of two surfaces of the object to be measured 102, a surface facing the light source 101 is referred to as a surface A, and a surface on the side of the ultrasonic wave transducer 103 is referred to as a surface B. In the object to be measured 102, a range to be measured is denoted by C. In the following description, it is assumed that the object to be measured 102 has a uniform thickness. It is also assumed that the object to be measured 102 is a living body. In the measurement system according to the present embodiment, information (in terms of a position, a shape, a type, etc.) about a particular substance existing in the object to be measured 102 is acquired using the photoacoustic effect. The light source 101 generates pulsed light at properly determined intervals. More particularly, in the present embodiment, light is emitted periodically (see FIG. 2A) in accordance with the driving signal 111 (see FIG. 2B) input to the light source 101. One reason why light is emitted periodically is that a mean value of small acoustic wave signals obtained via the measurement performed repeatedly can give improved detection accuracy. The emitted light illuminates the surface of the object to be measured 102 and the incident light propagates into the object to be measured 102. When the propagating light reaches a particular substance in the object to be measured 102, an acoustic wave is generated by the photoacoustic effect. The magnitude of the generated acoustic wave depends on the strength of the propagating light, the characteristics of the substance, the size of the substance, etc. If the ultrasonic wave transducer 103 receives generated acoustic wave, the ultrasonic wave transducer 103 outputs a detection signal 113 including information indicating the magnitude of the received acoustic wave.

As described above, the light incident on the object to be measured 102 generates great acoustic waves at the surfaces A and B of the object to be measured 102. That is, a great acoustic wave signal is generated at a skin or the like existing on the surface of the object to be measured 102. At the surface A, the incident light has not yet encountered attenuation that is going to occur in the object to be measured 102, and thus the incident light has a great intensity, which allows it to generate a great acoustic wave. Acoustic waves generated at various locations in the object to be measured 102 travel in the object to be measured 102 at a velocity specific to the object to be measured 102 while attenuating and finally the acoustic waves reach the ultrasonic wave transducer 103 after a travel of a particular time. Acoustic waves generated at locations closer to the ultrasonic wave transducer 103 arrive earlier.

Therefore, based on the time when each acoustic wave reaches the ultrasonic wave transducer 103, it is possible to determine the location where the acoustic wave was generated. In the measurement system according to the present embodiment, based on the difference in arrival time, information about the object to be measured 102 is obtained and the obtained information is used to generate information such as an image.

The acoustic waves reach the ultrasonic wave transducer 103 in the order described below. First, an acoustic wave generated at the surface B of the object to be measured 102 arrives. Next, acoustic waves generated in a measurement range C in the object to be measured 102 arrive. Finally an acoustic wave generated at the surface A of the object to be measured 102 arrives. That is, acoustic waves generated in the inside of the object to be measured 102 to be used in the measurement are detected as a signal located between the acoustic waves that are generated at the surfaces A and B and that are not used in the measurement (see FIG. 2C). The acoustic waves generated at the surfaces A and B of the object to be measured 102 are not only unnecessary but the acoustic waves may exert an influence on the receiving operation if the electromechanical transduction apparatus is in the receiving state when the acoustic waves arrive. After the acoustic wave generated at the surface B has arrived, the acoustic waves generated in the inside of the object to be measured 102 start to arrive, and thus the influence on the receiving operation can directly cause degradation of the reception characteristic for the acoustic waves to be measured. To avoid such degradation, in the present embodiment, the ultrasonic wave transducer 103 is not put in the receiving state except for a period in which the acoustic wave generated in an internal region of the object to be measured 102 arrives at the ultrasonic wave transducer 103. More specifically, the receiving state is enabled only for a particular period P after a particular transition period of time D has elapsed since each periodic emission of light from the light source 101 (see FIG. 2D).

The transition period D is set to be longer than a time needed for the acoustic wave generated at the surface B to reach the ultrasonic wave transducer 103. The period P is set to be shorter than a period from a time at which the acoustic wave generated at the surface B reaches the ultrasonic wave transducer 103 to a time at which the acoustic wave generated at the surface A reaches the ultrasonic wave transducer 103. By setting the transition period D and the period P, it becomes possible to put the ultrasonic wave transducer 103 in the non-receiving state over a period in which the acoustic waves generated at the surfaces of the object to be measured 102 arrive, and thus it becomes possible to prevent or suppress the influence of the large acoustic wave on the reception characteristic for the acoustic waves to be detected for the measurement. When the measurement of the acoustic waves to be measured is started, the ultrasonic wave transducer 103 is activated to receive the acoustic waves. This makes it possible to make a high-precision detection of the acoustic waves to be detected while suppressing the influence of the undesirable acoustic waves on the reception characteristic as described above. More specifically, the ultrasonic wave transducer 103 is controlled such that in accordance with the timing of outputting an electromagnetic wave, the ultrasonic wave transducer 103 is put in the non-receiving state for a first period D, the ultrasonic wave transducer 103 is put in the receiving state for a following second period P, and the ultrasonic wave transducer 103 is put in a non-receiving state for a third period.

In the setting, the transition period D and the period P may be calculated from known information about the thickness of the object to be measured and the velocity of the acoustic wave in the object to be measured, and the calculated values of the transition period D and the period P may be set in advance in the apparatus. Alternatively, the setting may be performed as follows. First, the apparatus is set to be in the receiving state for all periods to make it possible to measure periods from the time at which light is emitted to times at which the apparatus detects signals such as those shown in FIG. 2C. Subsequently, from the measurement result, the apparatus automatically sets the transition period D and the period P. After that, the apparatus starts actual measurement.

Figure 3A:
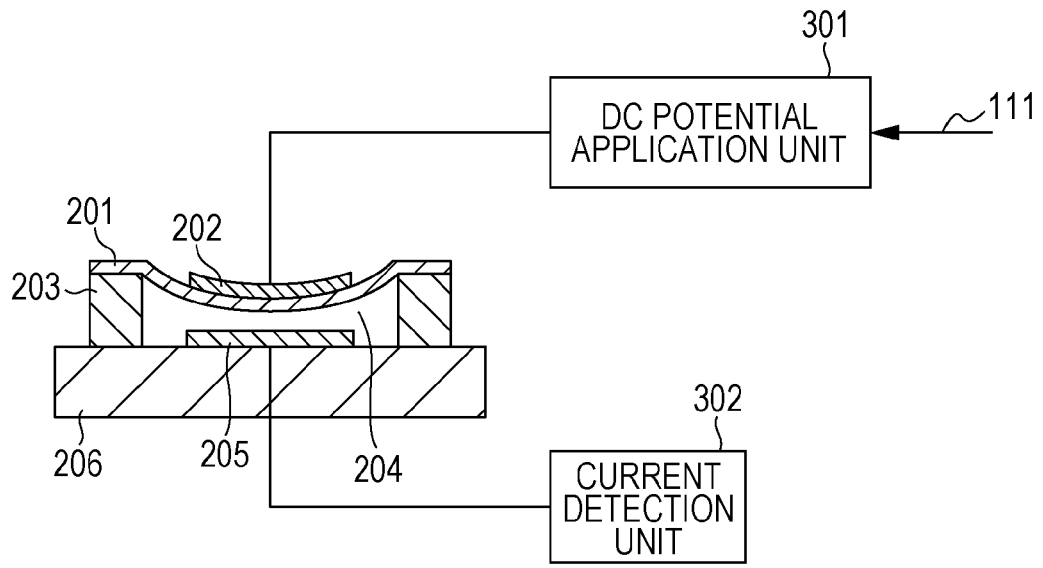
FIGS. 3A and 3B are diagrams illustrating an apparatus and a method of driving an electromechanical transduction apparatus according to an embodiment of the present invention.
Figure 3B:
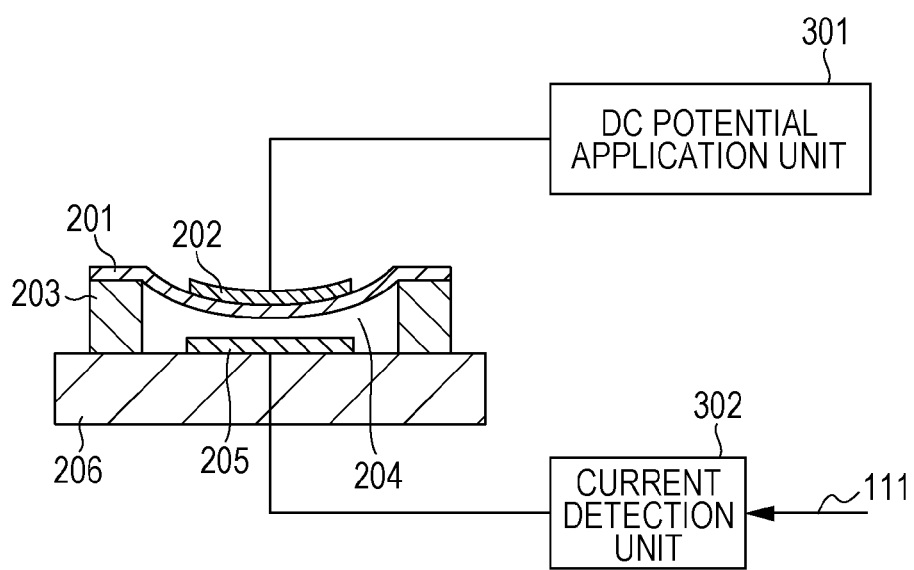

In the following explanation, it is assumed by way of example that a CMUT is used as the ultrasonic wave transducer 103. FIGS. 3A and 3B illustrate a configuration of the CMUT. In FIGS. 3A and 3B, reference numeral 201 denotes a vibrating membrane of a cell of the CMUT, reference numeral 202 denotes an upper electrode, reference numeral 203 denotes a supporting member that supports the vibrating membrane 201, reference numeral 204 denotes a gap (space), reference numeral 205 denotes a lower electrode, reference numeral 206 denotes a substrate, reference numeral 301 denotes a DC potential application unit, and reference numeral 302 denotes a current detection unit. In this CMUT, the upper electrode 202 is formed on the vibrating membrane 201 supported by the supporting member 203 formed on the substrate 206. The lower electrode 205 is disposed on the substrate 206 such that the lower electrode 205 opposes the upper electrode 202 on the vibrating membrane 201 via a gap 204 (normally, of 10 nm to 900 nm). A set of the two electrodes 202 and 205 opposing each other via the vibrating membrane 201 and the gap 204 is called a cell. The CMUT is a transducer array in which a plurality of (usually 100 to 3000) cells form one element (pixel) and there are 200 to 4000 elements in total. The CMUT generally has a size of 10 mm to 10 cm.

The upper electrode 202 is connected in common over the entire area of the CMUT. The upper electrode 202 is connected to the DC potential application unit 301 such that the DC potential application unit 301 applies a particular DC potential uniformly to the upper electrode 202 thereby producing a particular potential difference between the upper electrode 202 and the lower electrode 105. In this state, if the vibrating membrane 201 receives an acoustic wave, the vibrating membrane 201 vibrates depending on the magnitude of the acoustic wave. Thus, the acoustic wave is converted into the vibration of the vibrating membrane 201 supported by the supporting member 203. The vibration of the vibrating membrane 201 causes electrostatic induction to occur in the lower electrode 205. As a result, a small electric current occurs in the lower electrode 205. This current is detected by the current detection unit 302 connected to the lower electrode 205. Thus, a received signal corresponding to the acoustic wave is obtained. As described above, in the CMUT, a vibration is converted into a current by the upper electrode 202 and the lower electrode 205 on the vibrating membrane 201, and the current is converted into a detection signal by the current detection unit 202.

In the case where the acoustic wave with the large magnitude is input to the CMUT, a very great vibration and a correspondingly great current occur in the CMUT. However, in this state, the CMUT is in a condition optimized to receive and detect a change in acoustic wave with a small magnitude. Therefore, the large vibration or the large current can change an operating point of the CMUT, which can cause a great change in a conversion ratio of information (such as a current) or can cause some part to be saturated. It may take a certain time for the CMUT to return to a normal receiving state. This can degrade the acoustic wave reception characteristic of the CMUT.

In the present embodiment, the driving signal 111 for the light source 101 is input to the DC potential application unit 301 or the current detection unit 302. That is, the DC potential application unit 301 or the current detection unit 302 includes the above-described timing detection unit that receives the driving signal 111. In the DC potential application unit 301 or the current detection unit 302, switching between the receiving state and the non-receiving state is performed in synchronization with the inputting of the driving signal 111 to the light source 101 (or the in synchronization with emission of light from the light source 101). More specifically, the control unit disposed in the DC potential application unit 301 or the current detection unit 302 switches the state between the receiving state and the non-receiving state in synchronization with the emission of light from the light source 101 based on the detection result provided from the timing detection unit. The switching may be performed by changing the ratio at which the vibration of the vibrating membrane 201 is converted into the current, or the ratio at which the current is transmitted to the current detection unit 302, or the ratio at which the current is converted into the detection signal.

To change the ratio at which the vibration of the vibrating membrane 201 is converted into the current, the driving signal 111 of the light source 101 may be input to the DC potential application unit 301 (as in the configuration shown in FIG. 3A). To change the ratio at which the current is transmitted to the current detection unit 302 or the ratio at which the current is converted into the detection signal, the driving signal 111 of the light source 101 may be input to the current detection unit 302 (as in the configuration shown in FIG. 3B) By changing the ratio in the above-described manner, it is possible to suppress the adverse effect of the excess of the magnitude of the vibration or current conveying information in the CMUT on the receiving state of the CMUT.

By driving the capacitive electromechanical transduction apparatus in the above-described manner in the measurement using the photoacoustic effect, it is possible to suppress the influence of acoustic waves generated by objects other than the object to be measured on the reception characteristic for the acoustic wave to be detected. Note that although in the present embodiment it is assumed that an unnecessary signal originates from an acoustic wave generated at the surface of the object to be measured 102, the present invention is not limited to such a case. For example, the apparatus and method according to the present embodiment may be applied to a case where an unnecessary signal originates from an acoustic wave generated by another object located outside the object to be measured 102.

Second Embodiment

A second embodiment is described below with reference to FIGS. 4A and 4B. In the second embodiment, a further specific configuration is disclosed for the driving apparatus and the driving method of switching the state of the receiving operation between ON and OFF states (i.e., between the receiving state and the non-receiving state). Except for the above, the second embodiment is similar to first embodiment described above. In the second embodiment, the receiving operation state is turned on/off by changing the ratio at which the current is converted into the detection signal.

In the present embodiment, a transimpedance circuit is used as a current-voltage conversion circuit to convert a small change in current into a change in voltage. FIGS. 4A and 4B illustrate a configuration of the transimpedance circuit serving as the current detection unit 302 according to the present embodiment. In FIGS. 4A and 4B, reference numeral 401 denotes an operational amplifier, reference numerals 402 and 404 denote resistors, reference numerals 403 and 405 denote capacitors, and reference numeral 406 denotes a path closing unit serving as the control unit. In the configuration shown in FIGS. 4A and 4B, the operational amplifier 401 is connected to a positive power supply VDD and a negative power supply VSS. First, an operation of detecting a change in capacitance is described below. An inverting input terminal (−IN) of the operational amplifier 401 is connected to the lower electrode 205 of the CMUT. An output terminal (OUT) of the operational amplifier 401 is connected to the inverting input terminal (−IN) via the path closing unit 406 and a parallel connection of the resistor 402 and the capacitor 403 such that an output signal is fed back to the inverting input terminal (−IN). A non-inverting input terminal (+IN) of the operational amplifier 401 is connected to a ground terminal (GND) via a parallel connection of the resistor 404 and the capacitor 405. The ground terminal (GND) has a middle voltage between potentials of the positive power supply VDD and the negative power supply VSS. The resistors 402 and 404 have equal resistance, and capacitors 403 and 405 have equal capacitance determined to meet the specifications of the CMUT in terms of the current detection (in the normal receiving state).

Figure 4A:
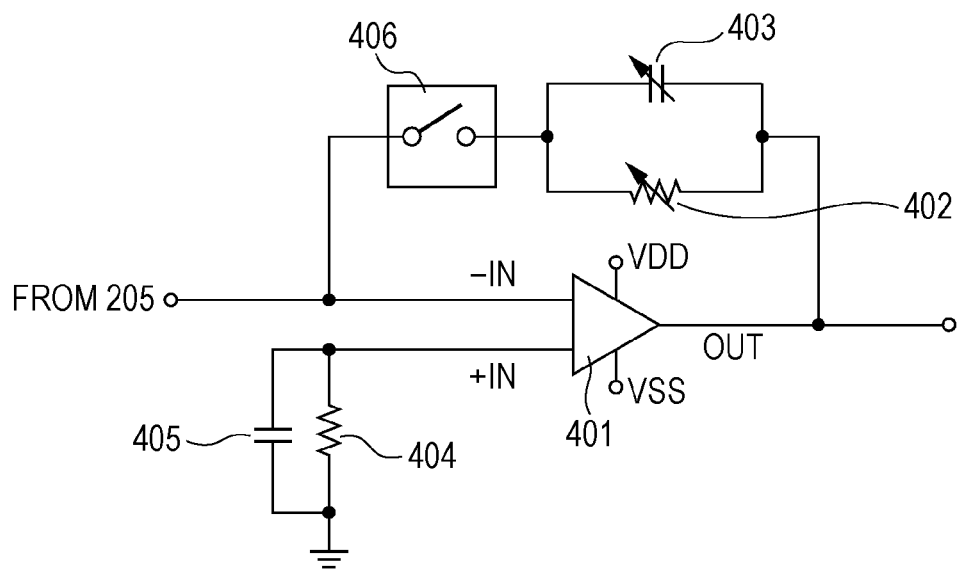
FIGS. 4A and 4B are diagrams illustrating an apparatus and a method of driving an electromechanical transduction apparatus according to an embodiment of the present invention.

When the ultrasonic wave transducer 103 is in the non-receiving state (OFF-state), the path closing unit 406 is controlled based on the detection result provided by the timing detection unit such that ends of two wirings in the path are not connected (i.e., they are opened) as shown in FIG. 4A. In this state, a current generated in the lower electrode 205 by the vibration of the vibrating membrane 201 does not flow through the feedback path of the operational amplifier 401 of the current detection unit 302. Thus, the transimpedance circuit serving as the current detection unit 302 does not output any detection signal regardless of the input current. Therefore, even when an unnecessary acoustic wave with a large amplitude is input, it is possible to prevent the current detection unit 302 from being saturated by the large current input to the current detection unit 302, which might make it impossible to acquire a detection signal over a particular period. It is also possible to prevent the large current input to the current detection unit 302 from exerting an influence on detection signals of other elements.

Figure 4B:
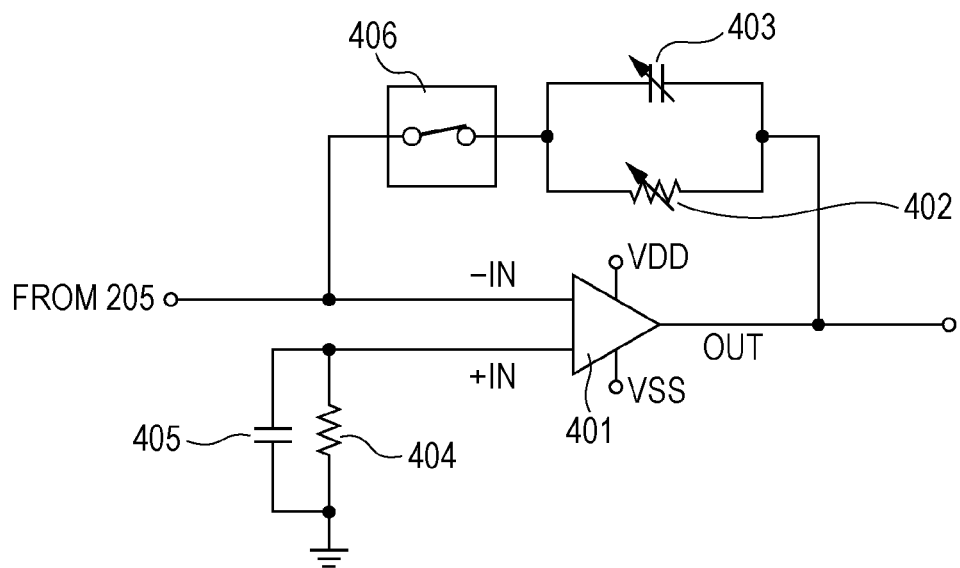

On the other hand, when the ultrasonic wave transducer 103 is in the receiving state (ON-state), the two ports of the path closing unit 406 is connected (short-circuited) as shown in FIG. 4B. In this state, when a current generated in the lower electrode 205 by a vibration of the vibrating membrane 201 flows into the current detection unit 302 via its input terminal, the current flows through the feedback path including the path closing unit 406 in the ON-state and the parallel connection of the resistor 402 and the capacitor 403. Thus, the transimpedance circuit serving as the current detection unit 302 outputs a detection signal corresponding to the input current, that is, the acoustic wave can be received. As described above, in synchronization with the outputting of the electromagnetic wave detected by the timing detection unit, the control unit (path closing unit 406) controls the current detection unit 302 configured to detect the induced current in the first electrode such that the induced current is detected in the receiving state while the induced current is not detected in the non-receiving state.

In the present embodiment, simply by inserting the path closing unit in the current detection unit 302, it is possible to realize the driving apparatus and driving method that allow the measurement using the photoacoustic effect to be performed in the receiving period without being significantly influenced in terms of the reception characteristic by acoustic waves generated by objects other than an object to be measured.

Third Embodiment

A third embodiment is described below with reference to FIGS. 5A and 5B. In this third embodiment, a further specific configuration is disclosed for the driving apparatus and the driving method of switching the state of the receiving operation between ON and OFF states (i.e., between the receiving state and the non-receiving state). In the third embodiment, the receiving operation state is switched between the ON-state and the OFF-state depending on whether a current generated in the lower electrode 205 by a vibration is input to the current detection unit 302 (i.e., depending on the ratio at which the current is transferred to the current detection unit 302).

Figure 5A:
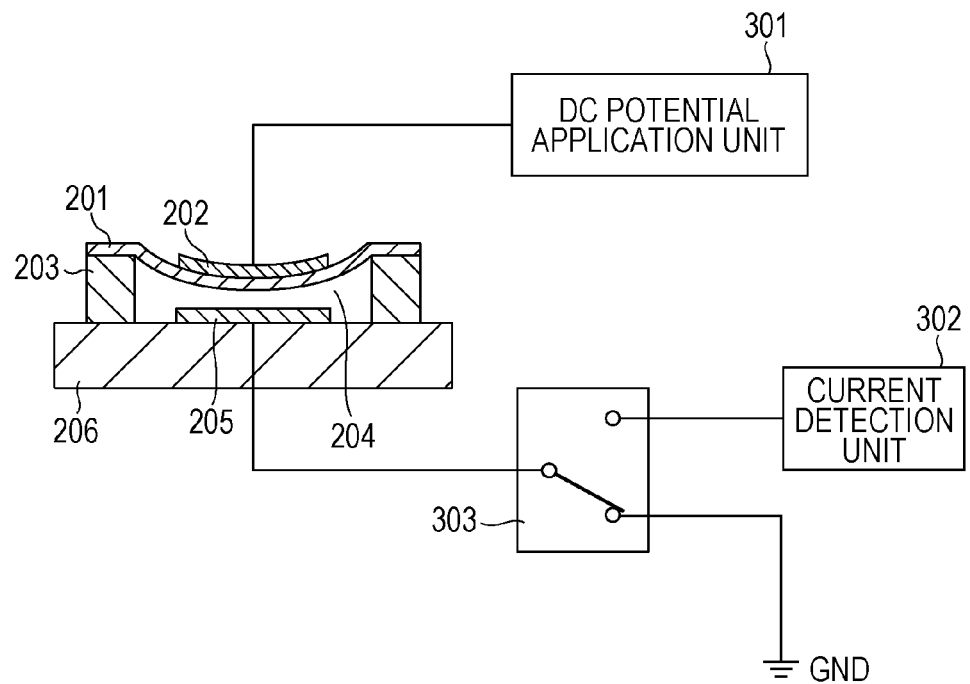
FIGS. 5A and 5B are diagrams illustrating an apparatus and a method of driving an electromechanical transduction apparatus according to an embodiment of the present invention.
Figure 5B:
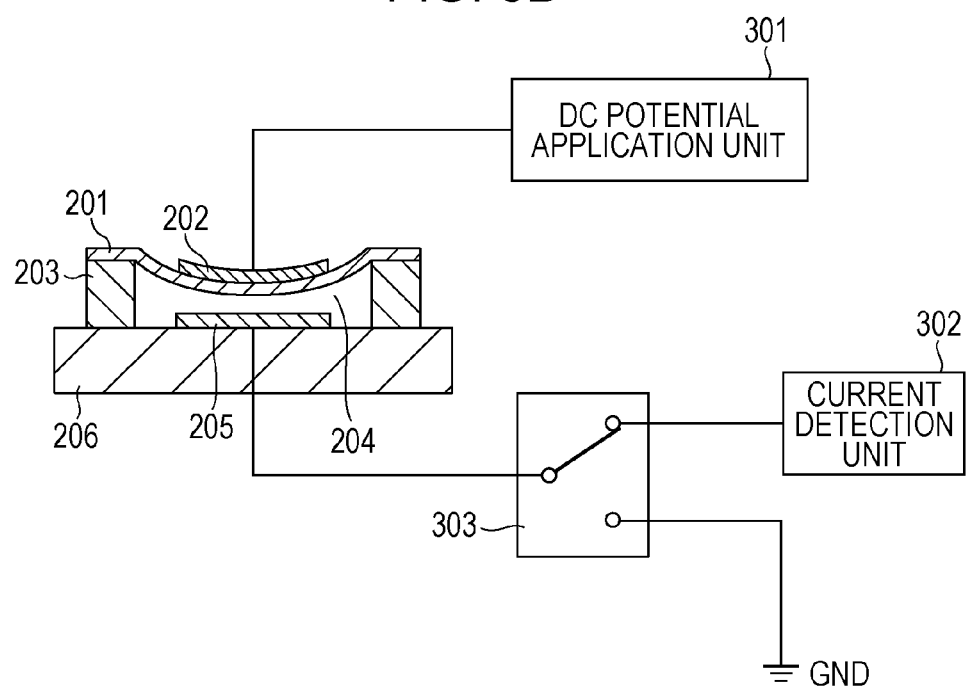

In FIGS. 5A and 5B showing a configuration of a CMUP according to the present embodiment, reference numeral 303 denotes a path switching unit serving as the control unit. In the present embodiment, the path switching unit 303 is disposed in a path between the lower electrode 205 and the current detection unit 302. The path switching unit 303 is configured to switch the connection of the lower electrode 205 between the input terminal of the current detection unit 302 and the ground terminal (GND). The ground terminal (GND) is set to be applied with a predetermined potential. When the CMUT is in the non-receiving state (OFF-state), the path switching unit 303 is controlled based on the detection result provided by the timing detection unit such that the connection is switched as shown in FIG. 5A. In this state, a current generated in the lower electrode 205 by a vibration of the vibrating membrane 201 flows into the ground terminal. Therefore, even when an unnecessary acoustic wave with a large amplitude is input, it is possible to prevent the current detection unit 302 from being saturated by the large current input to the current detection unit 302, which might make it impossible to acquire a detection signal over a particular period. It is also possible to prevent the large current input to the current detection unit 302 from exerting an influence on detection signals of other elements.

On the other hand, when the ultrasonic wave transducer 103 is in the receiving state (ON-state), the path switching unit 303 switches the connection as shown in FIG. 5B such that the current generated in the lower electrode 205 by the vibration of the vibrating membrane 201 flows into the input terminal of the current detection unit 302. Thus, the current detection unit 302 is allowed to detect a current signal corresponding to the magnitude of a received acoustic wave and output a resultant detection signal. In the above-described manner, the control unit (path switching unit 303) serving as the switch unit is controlled in synchronization with outputting of the electromagnetic wave detected by the timing detection unit. That is, in the receiving state, the control unit makes a connection between the first electrode and the current detection unit 302 that detects a current induced in the first electrode, while in the non-receiving state, the control unit disconnects the connection between the first electrode and the current detection unit 302 that detects a current induced in the first electrode.

In the present embodiment, simply by providing the path switching unit 303, it is possible to prevent the reception characteristic for an object to be measured from being significantly influenced by an acoustic wave generated by an object other than the to-be-measured object in measurement using the photoacoustic effect.

Fourth Embodiment

A fourth embodiment is described below with reference to FIGS. 6A and 6B. In this fourth embodiment, a further specific configuration is disclosed for the driving apparatus and the driving method of switching the state of the receiving operation between ON and OFF states (i.e., between the receiving state and the non-receiving state). In the fourth embodiment, the receiving operation state is turned on/off by changing the ratio at which a vibration of the vibrating membrane 201 is converted into a current.

Figure 6A:
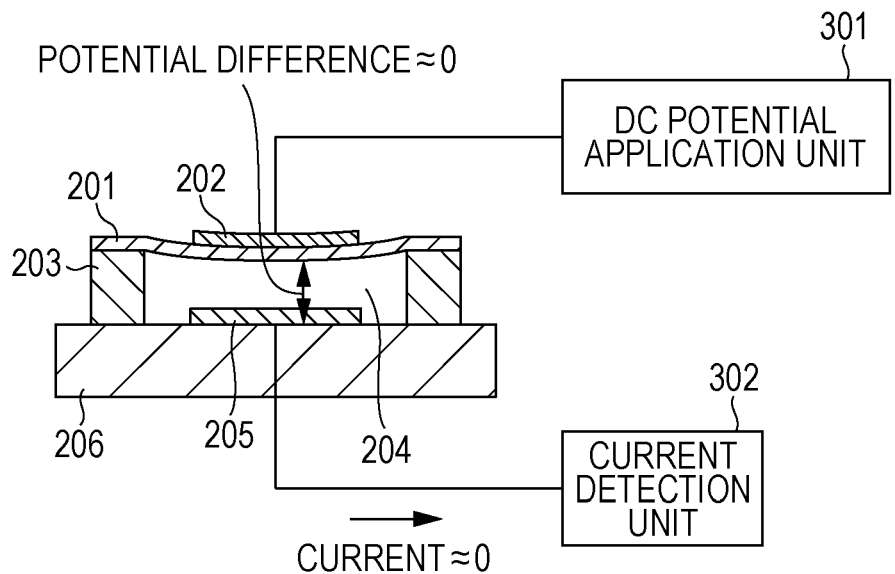
FIGS. 6A and 6B are diagrams illustrating an apparatus and a method of driving an electromechanical transduction apparatus according to an embodiment of the present invention.
Figure 6B:
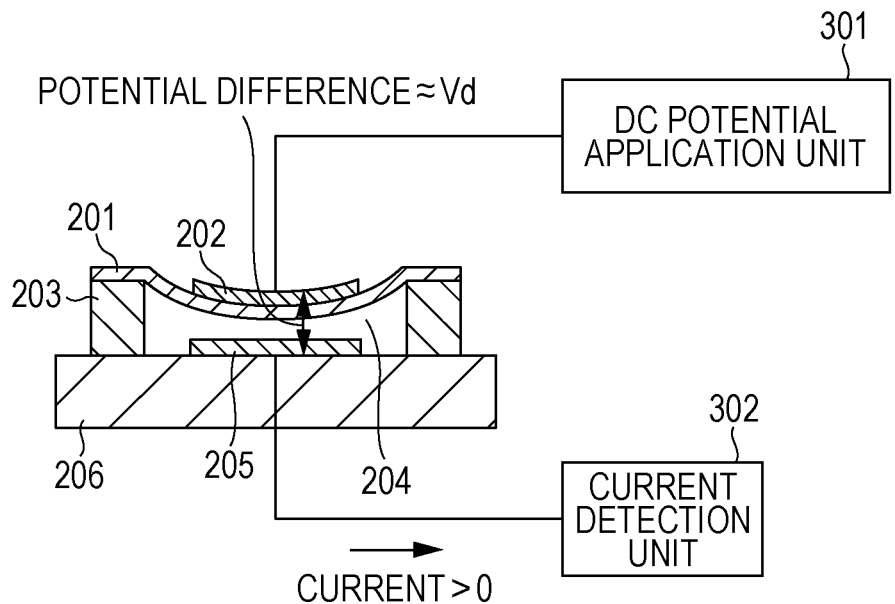

FIGS. 6A and 6B illustrate the position of the vibrating membrane 201 according to the present embodiment. FIGS. 2E and 2F indicate timings associated with the acoustic wave measurement system according to the present embodiment. In each of FIGS. 2E and 2F, a horizontal axis represents a time. In FIG. 2E, a vertical axis represents the potential difference between the electrodes 202 and 205, while a vertical axis represents the amount of bending of the vibrating membrane 201 in FIG. 2F. In the present embodiment, the ratio at which the vibration of the vibrating membrane 201 is converted into a current is changed by changing the potential difference applied between the upper electrode 202 and the lower electrode 205 by the control unit in the DC potential application unit 301 according to a detection result provided by the timing detection unit. More specifically, when the potential difference is set to be substantially 0, the vibrating membrane 201 is put in a state in which the vibrating membrane 201 has substantially no bending as shown in FIG. 6A and the CMUT serving as the ultrasonic wave transducer 103 is in the non-receiving state (OFF-state). On the other hand, when the potential difference is set to be equal to a predetermined value Vd, the vibrating membrane 201 is put in a state in which the vibrating membrane 201 is bent toward the lower electrode 205 as shown in FIG. 6B and the CMUT is brought into the receiving state (ON-state). These two states are described in further detail below.

When the CMUT is in the non-receiving state (OFF-state), the potential difference between the upper electrode 202 and the lower electrode 205 is substantially equal to 0, and the vibrating membrane 201 is slightly bent toward the substrate 206. This slight bending occurs because the gap 204 of the cell is evacuated to a pressure lower than the atmospheric pressure and thus the vibrating membrane 201 is slightly bent to the substrate 206 by a force produced by the difference between the internal pressure of the gap 204 and the atmospheric pressure. The amount of bending of the vibrating membrane 201 depends on a mechanical characteristic of the vibrating membrane 201 determined by parameters including its size, shape, thickness, membrane quality, etc. When an acoustic wave is received, the magnitude of a small current detected is inversely proportional to the distance between the electrodes 202 and 205 and is proportional to the potential difference between the electrodes 202 and 205. In the present state, the bending of the vibrating membrane 201 is slight, the distance between the electrodes is great, and the potential difference is substantially equal to 0, and thus substantially no current is created by a vibration of the vibrating membrane 201 produced by the received acoustic wave. That is, the ratio at which the vibration of the vibrating membrane 201 is converted into the current is substantially equal to 0, and thus no detection signal corresponding to the received acoustic wave is output. That is, the CMUT can be regarded in the non-receiving state.

On the other hand, when the CMUT is in the receiving state (ON-state), the potential difference between the upper electrode 202 and the lower electrode 205 is set to be equal to the specific value Vd and thus the vibrating membrane 201 is further bent toward the substrate 206. This further bending occurs because the specific potential difference Vd applied between the upper electrode 202 and the lower electrode 205 creates an electrostatic attractive force between the two electrodes and thus the vibrating membrane 201 is greatly attracted toward the substrate 206. Note that the amount of bending is set to be equal or less than one-third the original distance between the upper electrode 202 and the lower electrode 205. If the potential difference is set to be too great, there is a possibility that the vibrating membrane 201 is greatly bent due to the electrostatic attractive force beyond one-third the original distance between the two electrodes and the vibrating membrane 201 may come into contact with the lower electrode 205. In the collapsed state in which the vibrating membrane 201 is in contact with the lower electrode 205, a great change occurs in the vibration characteristic of the vibrating membrane 201 or a capacitance characteristic, and thus a great undesirable change occurs in the acoustic wave reception characteristic of the CMUT.

As described above, when the potential difference applied between the upper electrode 202 and the lower electrode 205 is increased, the electrostatic attractive force between the two electrodes increases and the bending of the vibrating membrane 201 increases, and thus the distance between the two electrodes decreases. The smaller the distance between the two electrodes, the greater current is generated in the lower electrode 205 by the same vibration of the vibrating membrane 201. Furthermore, the greater potential difference between the two electrodes leads to a further increase in the current. That is, the CMUT is put into a state in which the vibration of the vibrating membrane 201 is converted into the current at an increased ratio. Thus, the CMUT is in the receiving state that is suitable for receiving acoustic waves. As described above, the control unit in the DC potential application unit 301 controls the potential difference between the two electrodes in synchronization with the outputting of the electromagnetic wave detected by the timing detection unit such that the potential difference in the non-receiving state is smaller than the potential difference in the receiving state and thus the current induced in the lower electrode 205 by the vibration of the upper electrode 202 in the non-receiving state is smaller than is induced in the receiving state.

In the present embodiment, the control unit in the DC potential application unit 301 controls the potential difference between the upper electrode 202 and the lower electrode 205 in synchronization with emission of light by the light source 101 such that the potential difference is switched between 0 and Vd at proper intervals (more specifically, periodically in synchronization with periodic emission of light by the light source 101 (see FIG. 2E)). Note that the frequency associated with a signal change in switching transition periods (a rising time and a falling time) may be set to be out of a frequency range in which vibrating membrane 201 is responsible to prevent the vibrating membrane 201 from vibrating due to a change in potential difference. In response to the change in potential difference between 0 and Vd, the amount of bending of the vibrating membrane 201 changes periodically as shown in FIG. 2E. This causes a periodic change in ratio at which the vibration of the vibrating membrane 201 is converted into the current, which results in suppression in reception of unnecessary acoustic waves.

In the present embodiment, as described above, simply by changing the potential applied to the upper electrode 202 of the CMUT by the control unit in the DC potential application unit 301, it is possible to switch the state of the CMUT between the receiving state and the non-receiving state. When the CMUT is in the non-receiving state, because the amount of bending of the vibrating membrane 201 is slight, input of an unnecessary acoustic wave with a large amplitude does not cause the vibrating membrane 201 to be brought into a collapsed state which would result in a great change in the state of the vibrating membrane 201. Even if an unnecessary acoustic wave with a large amplitude is input and the vibrating membrane 201 greatly vibrates, the vibration produces substantially no current in the lower electrode 205. Thus, it is possible to prevent the current detection unit 302 from being saturated by a large input current, which would make it impossible to obtain a detection signal for a particular period. It is also possible to prevent detection signals of other elements from being influenced by a large current input to the current detection unit 302.

In the present embodiment, simply by changing a potential applied to the electrode without having to providing an additional part or a process, it is possible to prevent the reception characteristic from being significantly influenced by an acoustic wave generated by an object other than the to-be-measured object in measurement using the photoacoustic effect, and thus it becomes possible to accurately detect an acoustic wave to be detected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-062602 filed Mar. 18, 2010, which is hereby incorporated by reference herein in its entirety.

What is claimed is:

1. An apparatus configured to drive a transduction apparatus, including a cell with a first electrode and a second electrode disposed so as to oppose each other via a gap, configured to receive an acoustic wave generated in an object irradiated with a pulsed light, the apparatus comprising:
   a timing detector configured to detect a timing of outputting of the pulsed light periodically from a light source; and
   a current detection unit configured to detect a current signal that is output from the first electrode by receiving the acoustic wave that is generated by the pulsed light,
   wherein the current detection unit converts the current signal into a voltage signal,
   wherein the first electrode outputs a first current signal for at least some time during a predetermined period from the timing of outputting of the pulsed light, and
   wherein the current detection unit doesn't convert the first current signal.

2. The apparatus according to claim 1, wherein the current detection unit is switched from a status of not converting the current signal to a status of converting the current signal in a cycle of a generating period of the pulsed light.

3. The apparatus according to claim 1, further comprising:
   a path switching unit disposed between the current detection unit and the first electrode,
   wherein the path switching unit does not connect the first electrode to the current detection unit during the predetermined period from the timing of outputting of the pulsed light; and wherein the path switching unit connects the first electrode to the current detection unit after the predetermined period elapses.

4. The apparatus according to claim 1, wherein the predetermined period is longer than a time for the acoustic wave generated at a surface of the object on the side of the transduction apparatus to reach the transduction apparatus, from the timing of outputting of the pulsed light.

5. The apparatus according to claim 1, wherein the timing detector is configured to detect the timing of outputting of the pulsed light based on a received driving signal of the light source.

6. The apparatus according to claim 1, wherein the timing detector is configured to receive a part of the pulsed light and detect the timing of outputting of the pulsed light based on a received pulsed light.

7. A measurement system comprising the apparatus according to claim 1 and a light source.

8. The apparatus according to claim 1,
wherein the first electrode outputs a second current signal after the predetermined period elapses from the timing of outputting of the pulsed light, and
wherein the current detection unit converts the second current signal.

9. The apparatus according to claim 1, further comprising:
a voltage application unit configured to adjust a potential difference between the first electrode and the second electrode,
wherein the voltage application unit applies a potential difference other than 0 between the first electrode and the second electrode during the predetermined period.

10. The apparatus according to claim 1,
wherein the current detection unit includes a current-voltage conversion circuit including a feedback unit and a path switching unit that is disposed between the feedback unit and the first electrode,
wherein the path switching unit does not connect the first electrode to the feedback unit during the predetermined period, and
wherein the path switching unit connects the first electrode to the feedback unit after the predetermined period elapses.

11. An apparatus configured to drive a transduction apparatus, including a plurality of cells each of which includes a first electrode and a second electrode disposed so as to oppose each other via a gap, configured to receive an acoustic wave generated in an object irradiated with a pulsed light, the apparatus comprising:
a voltage application unit configured to adjust a potential difference between the first electrode and the second electrode; and
a timing detector configured to detect a timing of outputting of the pulsed light from a light source,
wherein the voltage application unit is connected to the second electrode that is electrically connected in all the plurality of cells included in the transduction apparatus, and
wherein, in all the plurality of cells, the voltage application unit makes a potential difference between the first electrode and the second electrode a first predetermined value during a predetermined period from the timing of outputting of the pulsed light.

12. The apparatus according to claim 11, wherein the predetermined period is longer than a time for the acoustic wave generated at a surface of the object on the side of the transduction apparatus to reach the transduction apparatus, from the timing of outputting of the pulsed light.

13. The apparatus according to claim 11, wherein the timing detector is configured to detect the timing of outputting of the pulsed light based on a received driving signal of the light source.

14. A measurement system comprising the apparatus according to claim 11 and a light source.

15. The apparatus according to claim 11,
wherein the first predetermined value is 0 or approximately 0.

16. The apparatus according to claim 11,
wherein after the predetermined period elapses from the timing of outputting of the pulsed light, the voltage application unit makes the potential difference between the first electrode and the second electrode a second predetermined value larger than an absolute value of the first predetermined value at the same time in all the plurality of cells.

17. The apparatus according to claim 16,
wherein each of the plurality of cells includes a vibrating membrane disposed at the second electrode, and
wherein the second predetermined value is smaller than a potential difference that causes the vibrating membrane and the first electrode to come into contact with each other.

18. A method of driving a transduction apparatus, including a cell with a first electrode and a second electrode disposed so as to oppose each other via a gap, configured to receive an acoustic wave generated in an object irradiated with a pulsed light, the method comprising:
detecting a timing of outputting of the pulsed light periodically from a light source; and
detecting a current signal that is output from the first electrode by receiving the acoustic wave that is generated by the pulsed light,
wherein the detecting comprises converting the current signal into a voltage signal, and
wherein a first current signal that is output from the first electrode for at least some time during a predetermined period from the timing of outputting of the pulsed light is not converted.

19. The method according to claim 18, further comprising switching from a status of not detecting the current signal to a status of detecting the current signal in a cycle of a generating period of the pulsed light.

20. The method according to claim 18, wherein the detecting is performed such that a driving signal of a light source or the pulsed light from the light source is detected thereby detecting the timing of the outputting of the pulsed light.

21. The method according to claim 18, wherein the controlling is performed such that the transduction apparatus is put in the non-receiving state for a first period following the timing of outputting the pulsed light, in the receiving state for a second period following the first period, and in the non-receiving state for a third period following the second period.

22. The method according to claim 18, wherein the predetermined period is longer than a time for the acoustic wave generated at a surface of the object on the side of the transduction apparatus to reach the transduction apparatus, from the timing of outputting of the pulsed light.

23. An apparatus configured to drive a transduction apparatus, including a first electrode and a second electrode disposed so as to oppose each other, configured to receive an acoustic wave generated in an object irradiated with a pulsed light, the apparatus comprising:

a timing detector configured to detect a timing of outputting of the pulsed light periodically from a light source; and a current detection unit configured to detect a current signal that is an output from the first electrode by receiving the acoustic wave that is generated by the pulsed light, wherein the first electrode outputs a first current signal for at least some time during a predetermined period from the timing of outputting of the pulsed light, and wherein the current detection unit doesn't detect the first current signal.

24. The apparatus according to claim 23, wherein the predetermined period is longer than a time for the acoustic wave generated at a surface of the object on the side of the transduction apparatus to reach the transduction apparatus, from the timing of outputting of the pulsed light.

25. The apparatus according to claim 23, wherein the output from the first electrode is electric current.

26. A measurement system comprising the apparatus according to claim 23 and a light source.

27. The apparatus according to claim 23,
wherein the first electrode outputs a second current signal after the predetermined period elapses from the timing of outputting of the pulsed light, and
wherein the current detection unit detects the second current signal.

28. The apparatus according to claim 23, further comprising:

a voltage application unit configured to adjust a potential difference between the first electrode and the second electrode, wherein the voltage application unit applies a potential difference other than 0 between the first electrode and the second electrode during the predetermined period.

29. The apparatus according to claim 23, further comprising:

a path switching unit disposed between the current detection unit and the first electrode, wherein the path switching unit does not connect the first electrode to the current detection unit during the predetermined period from the timing of outputting of the pulsed light, and wherein the path switching unit connects the first electrode to the current detection unit after the predetermined period elapses.

30. The apparatus according to claim 23,
wherein the current detection unit includes a current-voltage conversion circuit including a feedback unit and a path switching unit that is disposed between the feedback unit and the first electrode, wherein the path switching unit does not connect the first electrode to the feedback unit during the predetermined period, and wherein the path switching unit connects the first electrode to the feedback unit after the predetermined period elapses.

* * * * *